US011913862B2

(12) United States Patent
Kitagawa et al.

(10) Patent No.: US 11,913,862 B2
(45) Date of Patent: Feb. 27, 2024

(54) CORE-SHELL PARTICLES, AND METHOD FOR SEPARATING AND PURIFYING SUBSTANCE TO BE SEPARATED USING CORE-SHELL PARTICLES

(71) Applicant: SANYO CHEMICAL INDUSTRIES, LTD., Kyoto (JP)

(72) Inventors: Takahiro Kitagawa, Kyoto (JP); Masumi Ueda, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 636 days.

(21) Appl. No.: 16/972,857

(22) PCT Filed: Jun. 7, 2019

(86) PCT No.: PCT/JP2019/022773
§ 371 (c)(1),
(2) Date: Dec. 7, 2020

(87) PCT Pub. No.: WO2019/240045
PCT Pub. Date: Dec. 19, 2019

(65) Prior Publication Data
US 2021/0247278 A1     Aug. 12, 2021

(30) Foreign Application Priority Data

Jun. 14, 2018   (JP) .................... 2018-113478

(51) Int. Cl.
| | | |
|---|---|---|
| *G01N 1/40* | (2006.01) | |
| *B01J 20/06* | (2006.01) | |
| *B01J 20/10* | (2006.01) | |
| *B01J 20/28* | (2006.01) | |
| *B03C 1/01* | (2006.01) | |
| *B03C 1/28* | (2006.01) | |

(52) U.S. Cl.
CPC .............. *G01N 1/405* (2013.01); *B01J 20/06* (2013.01); *B01J 20/103* (2013.01); *B01J 20/28007* (2013.01); *B01J 20/28009* (2013.01); *B01J 20/28021* (2013.01); *B03C 1/01* (2013.01); *B03C 1/28* (2013.01); *G01N 1/4077* (2013.01); *B03C 2201/18* (2013.01); *B03C 2201/26* (2013.01)

(58) Field of Classification Search
CPC .... B01J 20/06; B01J 20/103; B01J 20/28009; B01J 20/28007; B01J 20/3204; B01J 20/3274; B01J 20/3293
See application file for complete search history.

(56) References Cited

U.S. PATENT DOCUMENTS

| | | | |
|---|---|---|---|
| 2003/0031783 A1* | 2/2003 | Pryor .................. | B01J 20/3293 427/128 |
| 2006/0019098 A1 | 1/2006 | Chan et al. | |
| 2011/0054162 A1 | 3/2011 | Kim et al. | |
| 2013/0342069 A1 | 12/2013 | Rowe | |
| 2014/0154713 A1 | 6/2014 | Mizuno et al. | |
| 2019/0015815 A1* | 1/2019 | Lawrence ............ | B01J 20/3285 |

FOREIGN PATENT DOCUMENTS

| | | |
|---|---|---|
| CN | 103597353 | 2/2014 |
| JP | 2016-90570 | 5/2016 |
| JP | 2016-105066 | 6/2016 |
| WO | 2017/155870 | 9/2017 |

OTHER PUBLICATIONS

International Search Report dated Aug. 20, 2019 in International (PCT) Application No. PCT/JP2019/022773, with English translation.

* cited by examiner

*Primary Examiner* — Benjamin M Kurtz
(74) *Attorney, Agent, or Firm* — Wenderoth, Lind & Ponack, L.L.P.

(57) ABSTRACT

The present invention aims to provide core-shell particles that can be used in a method of separating a substance to be separated and that allow obtainment of a highly purified product. Each of a plurality of core-shell particles (C) of the present invention includes a core layer (P) as magnetic silica particles containing the magnetic metal oxide particles (A) and a shell layer (Q) that is a silica layer on a surface of the core layer (P), an average thickness of a plurality of shell layers (Q) being 3 to 3000 nm, wherein a weight percentage of the magnetic metal oxide particles (A) in the core layer (P) is 60 to 95 wt % based on a weight of the core layer (P), and the plurality of core-shell particles (C) have a particle size distribution with a coefficient of variation of 50% or less.

17 Claims, No Drawings

CORE-SHELL PARTICLES, AND METHOD FOR SEPARATING AND PURIFYING SUBSTANCE TO BE SEPARATED USING CORE-SHELL PARTICLES

TECHNICAL FIELD

The present invention relates core-shell particles and a separation and purification method of separating a substance to be separated using the core-shell particles.

BACKGROUND ART

Conventionally, purification methods using column chromatography have been used as methods of separating biological substances such as proteins. However, purification methods using column chromatography require large columns and a large amount of buffer to purify proteins or the like to a high level of purity, and take a long time for purification, resulting in high cost.

Thus, there has been disclosed a technique for purifying a protein using magnetic silica particles, as a technique that allows easy separation and recovery by a magnetic force (Patent Literature 1). However, a purified product obtained by this method contains a large amount of non-target proteins and thus lacks sufficient purity.

CITATION LIST

Patent Literature

Patent Literature 1: JP 2016-90570 A

SUMMARY OF INVENTION

Technical Problem

The present invention aims to provide core-shell particles that can be used in a method of separating a substance to be separated, the method being capable of providing a highly purified product.

Solution to Problem

As a result of extensive studies to solve the above problems, the present inventors arrived at the present invention.

Specifically, the present invention provides a plurality of core-shell particles (C), each core-shell particle (C) including:
  a core layer (P) as magnetic silica particles containing magnetic metal oxide particles (A); and,
  a shell layer (Q) that is a silica layer on a surface of the core layer (P), an average thickness of a plurality of shell layers (Q) being 3 to 3000 nm,
  wherein a weight percentage of the magnetic metal oxide particles (A) in the core layer (2) is 60 to 95 wt % based on a weight of the core layer (P), and
  the plurality of core-shell particles (C) have a particle size distribution with a coefficient of variation of 50% or less. The present invention also provides a separation and purification method of separating a substance to be separated (D) from a sample (E), which uses the plurality of core-shell particles (C).

Advantageous Effects of Invention

Use of the core-shell particles of the present invention to separate a substance to be separated from a sample allows obtainment of a highly purified product from the sample.

DESCRIPTION OF EMBODIMENTS

Each of a plurality of core-shell particles (C) of the present invention includes:
  a core layer (P) as magnetic silica particles containing magnetic metal oxide particles (A); and
  a shell layer (Q) that is a silica layer on a surface of the core layer (P), an average thickness of a plurality of shell layers (Q) being 3 to 3000 nm.

A weight percentage of the magnetic metal oxide particles (A) in the core layer (P) is 60 to 95 wt % based on a weight of the core layer (P).

The plurality of core-shell particles (C) have a particle size distribution with a coefficient of variation of 50% or less.

The core-shell particles (C) of the present invention are particularly applicable to a separation method of the present invention, i.e., "separation method of separating a substance to be separated (D) from a sample (E)" (described in detail later).

The substance to be separated (D) in the present invention refers to a target substance (D1) or a non-target substance (D2) in a mixture of multiple substances (e.g., biological substances) in the sample (E).

The target substance (D1) refers to a substance intended to be ultimately obtained as a purified product from the sample (E).

The non-target substance (D2) refers to a substance intended to be ultimately removed from the sample (E).

Here, examples of the sample (E) in the present invention include biological samples (e.g., biological fluids such as serum, blood, lymph, ascites, and urine, various types of cells, and culture solutions) and mixtures containing the target substance (D1) and/or the non-target substance (D2) (described in detail later).

As described above, each of the plurality of core-shell particles (C) of the present invention includes the core layer (P) as magnetic silica particles containing the magnetic metal oxide particles (A) and the shell layer (Q) that is a silica layer on the surface of the core layer (P), an average thickness of the plurality of shell layers (Q) being 3 to 3000 nm.

Preferably, the core layer (P) is a sphere containing the magnetic metal oxide particles (A) dispersed in a silica matrix.

The shell layer (Q) may contain a component other than silica.

The magnetic metal oxide particles (A) in the present invention may be ferrimagnetism, ferromagnetism, or superparamagnetism. Preferred of these is superparamagnetism because there is no residual magnetization derived from magnetic particles with superparamagnetism after magnetic separation. As a result, magnetic particles with superparamagnetism can be quickly re-dispersed. The term "superparamagnetism" is a phenomenon in which a substance induces a temporary magnetic field where individual atomic magnetic moments of the substance are aligned in the presence of an external magnetic field, and the substance loses its magnetic field due to partial misalignment that occurs in response to removal of the external magnetic field.

Examples of the magnetic metal oxide particles (A) include oxides of iron, cobalt, nickel, and alloys thereof. Iron oxides are particularly preferred because they have excellent sensitivity to a magnetic field. Each of the magnetic metal oxide particles (A) may be used alone or in combination of two or more thereof.

The iron oxide used in the magnetic metal oxide particles (A) may be selected from various known iron oxides. Preferred iron oxides are magnetite, γ-hematite, an intermediate iron oxide between magnetite and α-hematite, and an intermediate iron oxide between γ-hematite and α-hematite because they have especially excellent chemical stability. Magnetite is more preferred because it has a high saturation magnetization and excellent sensitivity to an external magnetic field.

The magnetic metal oxide particles (A) in the core layer (P) preferably have a volume average particle size of 1 to 50 nm, more preferably 1 to 30 nm, particularly preferably 1 to 20 nm.

The magnetic metal oxide particles (A) having a volume average particle size of 1 nm or more are easy to synthesize. The magnetic metal oxide particles (A) having a volume average particle size of 50 nm or less are easily dispersed uniformly in a silica matrix.

The volume average particle size of the magnetic metal oxide particles (A) in the present invention is defined as the volume average of particle sizes of any 200 magnetic metal oxide particles (A), measured by observation using a scanning electron microscope (e.g., "JSM-7000F" from JEOL Ltd.).

The volume average particle size of the magnetic metal oxide particles (A) can be controlled by adjusting the metal ion concentration during production of the magnetic metal oxide particles (A) (described later). The volume average particle size of the magnetic metal oxide particles (A) can also be set to a desired value by a method such as classification.

In the present invention, the lower limit of the weight percentage of the magnetic metal oxide particles (A) in one core layer (P) based on the weight of the core layer (P) is 60 wt %, preferably 65 wt %, and the upper limit thereof is 95 wt %, preferably 80 wt %.

When the weight percentage of the magnetic metal oxide particles (A) is less than 60 wt %, the resulting core-shell particles (C) have insufficient magnetism, requiring a longer separation operation in practical use. When the weight percentage of the magnetic metal oxide particles (A) is more than 95 wt %, synthesis thereof is difficult.

The magnetic metal oxide particles (A) may be produced by any method. For example, they can be synthesized by co-precipitation using water-soluble iron salts and ammonia based on the method of Massart (R. Massart, IEEE Trans. Magn. 1981, 17, 1247), or by a method utilizing oxidation in an aqueous solution of water-soluble iron salts.

As described above, the core-shell particles (C) of the present invention are particles each having a core-shell form in which the shell layer (Q) is formed on the surface of each core layer (P).

In the present invention, the average thickness of the shell layers (Q) can be measured by transmission electron microscopic observation of microtome cross sections of the core-shell particles (C) embedded in a resin (e.g., epoxy resin), and analyzing images obtained by the observation. The average thickness of the shell layers (Q) is defined as the average of the thicknesses of the shell layers (Q) of any 100 core-shell particles (C), measured by observation using a transmission electron microscope (e.g., "H-7100" from Hitachi, Ltd.). The thickness of the shell layer (Q) is defined as the average of the thinnest and thickest portions thereof in one core-shell particle (C).

The average thickness of the shell layers (Q) is 3 to 3000 nm, preferably 10 to 800 nm, more preferably 50 to 800 nm, particularly preferably 50 to 500 nm, most preferably 50 to 200 nm. The shell layers (Q) having an average thickness of less than 3 nm produce no effect, resulting in a smaller amount of the substance (D) separated. The shell layers (Q) having an average thickness of more than 3000 nm are difficult to synthesize.

The plurality of core-shell particles (C) have a volume average particle size of preferably 0.5 to 20 μm, more preferably 1 to 10 μm, particularly preferably 1.1 to 5 μm. The core-shell particles (C) having a volume average particle size of or 0.5 μm or more tend to reduce the time for separation and collection. The core-shell particles (C) having an average particle size of 20 μm or less can each have a relatively large specific surface area, resulting in a larger amount of the substance (D) separated, with a tendency of a higher binding efficiency.

Further, the separability of the substance to be separated (D) improves when the core-shell particles (C) have a volume average particle size of 1.1 μm or more and a particle size distribution with a coefficient of variation of 21 to 35% (described in detail later).

The term "separability" as used herein is described separately for the case when the substance to be separated (D) is the target substance (D1) and for the case when the substance to be separated (D) is the non-target substance (D2).

When the substance to be separated (D) is the target substance (D1), the expression "improve the separability" means that the target substance (D1) in a component extracted from the sample (E) using the core-shell particles (C) has a higher purity (proportion).

When the substance to be separated (D) is the non-target substance (D2), the expression "improve the separability" means that the proportion of the non-target substance (D2) is lower in a component after the non-target substance (D2) is removed from the sample (E) using the core-shell particles (C).

In the present invention, the volume average particle size of the core-shell particles (C) is the volume average particle size measured using, for example, a laser diffraction/scattering particle size distribution measuring device ("Microtrac MT3300" from MicrotracBEL Corp.).

The volume average particle size of the core-shell particles (C) can be controlled by controlling the volume average particle size of the core layers (P) and the average thickness of the shell layers (Q). The volume average particle size of the core layers (P) can be controlled by adjusting mixing conditions (e.g. shear strength) in production of an oil-in-water emulsion (described later) so as to adjust the particle size of the oil-in-water emulsion. The average thickness of the shell layers (Q) can be controlled by adjusting the amount of an (alkyl)alkoxysilane, the amount of a catalyst, reaction time, and the like during formation of the shell layers (Q) (described later).

The volume average particle size of the core layers (P) and the volume average particle size of the core-shell particles (C) can also be set to desired values by changing conditions in a water-washing step or by a method such as classification during production, for example.

In the present invention, the core-shell particles (C) have a particle size distribution with a coefficient of variation of 50% or less, as described above. A coefficient of variation of more than 50% results in poor separability of the substance to be separated (D).

In order to further improve the separability of the substance to be separated (D), the lower limit of the coefficient of variation of the particle size distribution of the core-shell particles (C) is preferably 10% or more, more preferably 13% or more, particularly preferably 20% or more, most preferably 21% or more.

In order to further improve the separability of the substance to be separated (D), the upper limit of the coefficient of variation of the particle size distribution of the core-shell particles (C) is 35% or less.

The coefficient of variation of the particle size distribution of the core-shell particles (C) can be measured by the following measurement method.

<Method of Measuring Coefficient of Variation>

The coefficient of variation in the present invention is a value that can be obtained by substituting a volume average particle size (d) and a standard deviation (SD), which are determined by a device such as a laser diffraction/scattering particle size distribution measuring device ("Microtrac MT3300" from MicrotracBEL Corp.), into a formula (1):

Coefficient of variation (%)=SD/$d$×100    (1).

The coefficient of variation of the particle size distribution of the core-shell particles (C) can be adjusted by classifying the core-shell particles.

For example, core-shell particles having a relatively large particle size can be removed by precipitating the particles by centrifugation. Core-shell particles having a relatively small particle size can be removed by removing the supernatant containing non-precipitated fine particles after centrifugation.

Preferably, the core-shell particles (C) of the present invention each have a ratio of the average thickness of the shell layers (Q) to the particle size of the core layer (P) (average thickness of shell layers (Q)/particle size of core layer (P)) of 0.001 to 10, more preferably 0.02 to 1.5, particularly preferably 0.04 to 1.5.

The separability of the substance to be separated (D) improves with a ratio of 0.001 or more.

The separability of the substance to be separated (D) improves with a ratio of 10 or less.

Here, in calculation of the ratio, a value determined by the method described above is used as the average thickness of the shell layers (Q). In calculation of the ratio, the particle size of the core layer (P) can be determined by the following calculation formula, using values of "the volume average particle size of the core-shell particles (C)" and "the average thickness of the shell layers (Q)" described above.

Particle size of core layer (P)=(volume average particle size of core-shell particles (C))−2×(average thickness of shell layers (Q))

The separability of the substance to be separated (D) improves significantly when the core-shell particles (C) have a ratio of the average thickness of the shell layers (Q) to the particle size of the core layer (P) (average thickness of shell layers (Q)/particle size of core layer (P)) of 0.02 to 1.5, and a particle size distribution with a coefficient of variation of 21 to 35%.

Next, a method of producing the core-shell particles (C) in the present invention is described.

The core-shell particles (C) in the present invention can be produced by a production method involving at least two steps described below.

(Step 1) A step of producing an oil-in-water emulsion of an (alkyl)alkoxysilane containing the magnetic metal oxide particles (A) to cause hydrolysis and polycondensation reaction of the (alkyl)alkoxysilane so as to produce the core layers (P) each in which the magnetic metal oxide particles (A) are embedded in silica (Step 2) A step of causing hydrolysis and polycondensation reaction of an (alkyl)alkoxysilane on the surface of each core layer (P) to form the shell layer (Q) thereon The above steps are described below.

First, step 1 is described.

Examples of the production method of the core layers (P) in the present invention include a method in which an oil-in-water emulsion is produced by mixing a dispersion (B1) containing the magnetic metal oxide particles (A) and an (alkyl)alkoxysilane in an amount of 30 to 1000 wt % based on the weight of the magnetic metal oxide particles (A) (hereinafter, such a dispersion is also simply referred to as the "dispersion (B1)") with a solution (B2) containing water, a nonionic surfactant, and a catalyst for hydrolysis of the (alkyl)alkoxysilane (hereinafter, such a solution is also simply referred to as the "the solution (B2)") to cause hydrolysis and polycondensation reaction of the (alkyl) alkoxysilane so as to produce particles each in which the magnetic metal oxide particles (A) are embedded in silica.

After the hydrolysis and polycondensation reaction of the (alkyl)alkoxysilane, the resulting product is subjected to solid-liquid separation by centrifugation and using a magnet or the like, whereby the core layers (P) are obtained.

In the above and below, the (alkyl)alkoxysilane refers to alkylalkoxysilane and/or alkoxysilane.

Examples of the (alkyl)alkoxysilane used include a compound represented by the following formula (1):

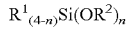

$R^1_{(4-n)}Si(OR^2)_n$    (1)

wherein $R^1$ and $R^2$ each represent a C1-C10 monovalent hydrocarbon group. One or more hydrogen atoms of the hydrocarbon group may be replaced by amino, carboxy, hydroxy, mercapto, or glycidyloxy groups.

Examples of the C1-C10 monovalent hydrocarbon group include C1-C10 aliphatic hydrocarbon groups (e.g., methyl, ethyl, n- or iso-propyl, n- or iso-butyl, n- or iso-pentyl, and vinyl groups), C6-C10 aromatic hydrocarbon groups (e.g., phenyl group), and C7-C10 aromatic-aliphatic groups (e.g., benzyl group).

In formula (1), n is an integer of 1 to 4. Use of an alkylalkoxysilane in which n is 1 requires use of an (alkyl) alkoxysilane in which n is 2 to 4 in combination. Preferably, n is 4 in terms of particle strength and amount of silanol groups on surfaces of the particles after the reaction.

Specific examples of the compound represented by formula (1) include alkoxysilanes (e.g., tetramethoxysilane, tetraethoxysilane, tetraisopropoxysilane, and tetrabutoxysilane); alkylalkoxysilanes (e.g., methyltrimethoxysilane and methyltriethoxysilane); alkylalkoxysilanes having an amino-substituted alkyl group (e.g., 3-aminopropyltrimethoxysilane, 3-aminopropylethoxysilane, N-(2-aminoethyl)-3-aminopropyltrimethoxysilane, and N-(2-aminoethyl)-3-aminopropyltriethoxysilane); alkylalkoxysilanes having a carboxy-substituted alkyl group (e.g., 7-carboxyheptyltriethoxysilane and 5-carboxy-pentyltriethoxysilane); alkylalkoxysilanes having a hydroxy-substituted alkyl group (e.g., 3-hydroxypropyltrimethoxysilane and 3-hydroxypropyltriethoxysilane); alkylalkoxysilanes having a mercapto-substituted alkyl group (e.g., 3-mercaptopropyltrimethoxysilane and 3-mercaptopropyltriethoxysilane); alkylalkoxysilanes having a glycidyloxy-substituted alkyl group (e.g., 3-glycidyloxypropyltrimethoxysilane and 3-glycidyloxypropyltriethoxysilane).

Each of these (alkyl)alkoxysilanes may be used alone or in combination of two or more thereof.

The amount of the (alkyl)alkoxysilane is preferably 30 to 1000 wt %, more preferably 40 to 500 wt %, relative to the weight of the magnetic metal oxide particles (A). Use of the (alkyl)alkoxysilane in an amount of 30 wt % or more relative to the weight of the magnetic metal oxide particles (A) facilitates uniform coating on surfaces of the magnetic metal oxide particles (A). Use of the (alkyl)alkoxysilane in an amount of 1000 wt % or less relative to the weight of the magnetic metal oxide particles (A) can reduce the time for collection by a magnetic force.

The amount of the water is preferably 500 to 50000 wt %, more preferably 1000 to 10000 wt %, relative to the weight of the magnetic metal oxide particles (A).

Further, synthesis of the core layers (P) may include adding a water-soluble organic solvent or the like to the solution (B2) or the like.

Examples of the water-soluble organic solvent include those having a solubility in water at 25° C. of 100 g/100 g of water or higher, such as C1-C4 monohydric alcohols (e.g., methanol, ethanol, and n- or iso-propanol), C2-C9 glycols (e.g., ethylene glycol and diethylene glycol), amides (e.g., N-methylpyrrolidone), ketones (e.g., acetone), cyclic ethers (e.g., tetrahydrofuran and tetrahydropyran), lactones (e.g., γ-butyrolactone), sulfoxides (e.g., dimethylsulfoxide), and nitriles (e.g., acetonitrile).

Preferred of these are C1-C4 monohydric alcohols for a uniform particle size of the core-shell particles (C). Each of these water-soluble organic solvents may be used alone or in combination of two or more thereof.

The amount of the water-soluble organic solvent is preferably 100 to 500 wt % relative to the weight of the water.

Examples of the nonionic surfactant include:
adducts of alkylene oxides (hereinafter, an alkylene oxide is abbreviated to "AO") with C8-C24 monohydric alcohols (e.g., decyl alcohol, dodecyl alcohol, coconut oil alkyl alcohol, octadecyl alcohol, and oleyl alcohol);
adducts of AO with C3-C36 dihydric to octahydric alcohols (e.g., glycerol, trimethylolpropane, pentaerythritol, sorbitol, and sorbitan);
adducts of AO with alkylphenols having a C6-C24 alkyl group (e.g., octylphenol and nonylphenol);
adducts of ethylene oxide with polypropylene glycol, and adducts of propylene oxide with polyethylene glycol;
adducts of AO with C8-C24 fatty acids (e.g., decanoic acid, lauric acid, myristic acid, palmitic acid, stearic acid, oleic acid, and coconut oil fatty acid);
fatty acid esters of the C3-C36 dihydric to octahydric alcohols and AO adducts thereof (e.g., TWEEN® 20 and TWEEN® 80);
alkyl glucosides (e.g., N-octyl-β-D-maltoside, n-dodecanoylsucrose, and n-octyl-β-D-glucopyranoside); and
fatty acid esters of sucrose, fatty acid alkanolamides, and AO adducts thereof (e.g., polyoxyethylene fatty acid alkanolamides).

Each of these may be used alone or in combination of two or more thereof.

Examples of the AO in the description of the nonionic surfactant include ethylene oxide, propylene oxide, and butylene oxide. The AO may be added in the form of either block or random.

The number of moles of AO added is preferably 1 to 50, more preferably 1 to 20, per mole of alcohol, phenol, or fatty acid.

In terms of solubility in water and viscosity, preferred of these nonionic surfactants are adducts of 1 to 50 mol (preferably 1 to 20 mol) ethylene oxide with a C8-C24 monohydric alcohol, such as polyoxyethylene alkyl ether and polyoxyethylene alkyl ether.

In order to improve the separability of the substance to be separated (D) upon separation and purification using the ultimately obtained core-shell particles (C), preferred of these nonionic surfactants are adducts of 1 to 50 mol (preferably 1 to 20 mol) ethylene oxide with a monohydric alcohol having a C8-C24 alkenyl group (e.g., oleyl alcohol).

The amount of the nonionic surfactant is 10 to 1000 wt %, more preferably 100 to 500 wt %, relative to the weight of the magnetic metal oxide particles (A). Use of the nonionic surfactant in an amount of 10 wt % or more or 1000 wt % or less relative to the weight of the magnetic metal oxide particles (A) tends to stabilize the emulsion and narrow the particle size distribution of the resulting particles.

The amount of the solution (B2) used in step 1 is preferably 1000 to 10000 wt %, more preferably 1500 to 4000 wt %, relative to the weight of the magnetic metal oxide particles (A) in the dispersion (B1).

Use of an aqueous solution containing the nonionic surfactant in an amount of 1000 wt % or more or 10000 wt % or less relative to the weight of the magnetic metal oxide particles (A) tends to stabilize the emulsion and narrow the particle size distribution of the resulting particles.

The catalyst for hydrolysis of the (alkyl)alkoxysilane can be a Lewis acid or a hydrochloric acid, for example. Specific examples thereof include inorganic acids (e.g., hydrochloric acid), organic acids (e.g., acetic acid), inorganic base compounds (e.g., ammonia), and amine compounds (e.g., ethanolamine).

The amount of the catalyst for hydrolysis is preferably 1 to 1000 wt %, more preferably 2 to 500 wt %, relative to the weight of the (alkyl)alkoxysilane.

The dispersion (B1) and the solution (B2) may be mixed by any method. They can be collectively mixed using an apparatus (described later), but it is preferred to add the dispersion (B1) dropwise to the solution (B2) under stirring for a uniform particle size of the core-shell particles (C).

The apparatus for mixing the dispersion (B1) with the solution (B2) may be any commercially available emulsifier or disperser. Examples thereof include batch-type emulsifiers such as IKA Homogenizer (IKA), Polytron (Kinematica), and TK Auto Homomixer (PRIMIX Corporation); continuous-type emulsifiers such as Ebara Milder (Ebara Corporation), TK Fill Mix, TK Pipeline Homomixer (PRIMIX Corporation), a colloid mill (Kobelco Eco-Solutions Co., Ltd.), Clearmix (M Technique Co., Ltd.), Slasher and Trigonal wet-type griding machines (Nippon Coke & Engineering, Co., Ltd.), Cavitron (Eurotec Co., Ltd.), and Fine Flow Mill (Pacific Machinery & Engineering Co., Ltd.); high-pressure emulsifiers such as Microfluidizer (Mizuho Industrial Co., Ltd.), Nanomizer Inc. (Nanomizer Inc.), and APV Gaulin (Gaulin); membrane emulsifiers such as a membrane emulsifier (REICA Co., Ltd.); vibration-type emulsifiers such as Vibromixer (REICA Co., Ltd.); and ultrasonic emulsifiers such as an ultrasonic homogenizer (Branson).

Preferred of these are APV Gaulin, IKA homogenizer, TK Auto Homomixer, Ebara Milder, TK Fill Mix, TK Pipeline Homomixer, and Clearmix (M Technique) for a uniform particle size.

The temperature of hydrolysis and polycondensation reaction of the (alkyl) alkoxysilane is preferably 10° C. to 100° C., more preferably 25° C. to 60° C. The reaction time is preferably 0.5 to 5 hours, more preferably 1 to 2 hours.

Next, step 2 is described.

Examples of the method of forming the shell layers (Q) in the present invention include a method in which the core layers (P) obtained in step 1, an (alkyl)alkoxysilane, a catalyst for hydrolysis of the (alkyl)alkoxysilane, water, and if necessary, a water-soluble organic solvent are mixed together to cause hydrolysis and polycondensation reaction of the (alkyl)alkoxysilane, whereby the shell layers (Q) containing silica are formed on the surfaces of the respective core layers (P).

Examples of the (alkyl)alkoxysilane hydrolysis used in step 2 include those exemplified in the description of step 1. Preferred examples are also the same as those described above.

In the reaction to form the shell layers (Q), the concentration of the core layers (P) is preferably less than 50 wt %, more preferably less than 20 wt %, based on the weight of the reaction solution.

The core layers (P) having a concentration of less than 50 wt % are uniformly dispersed in the solution. This facilitates uniform formation of the shell layers (Q), and can prevent or reduce silica-mediated aggregation of the core layers (P).

In the reaction to form the shell layer (Q), the concentration of the (alkyl)alkoxysilane is preferably less than 50 wt %, more preferably less than 20 wt %, based on the weight of the reaction solution.

A concentration of the (alkyl)alkoxysilane of less than 50 wt % in the solution can prevent or reduce silica-meditated aggregation of the core layers (P), and can also prevent or reduce generation of particles consisting of silica, aggregates of such particles, and aggregates consisting of such particles and the core layers (P).

Example of the catalyst for hydrolysis of the (alkyl) alkoxysilane used in step 2 include those exemplified in the description of step 1.

The amount of the catalyst for hydrolysis is preferably 1 to 2000 wt %, more preferably 2 to 1000 wt %, relative to the weight of the (alkyl)alkoxysilane.

The amount of the water is preferably 0.01 to 99.9 wt %, more preferably 0.1 to 99.9 wt %, relative to the weight of the reaction solution (the total weight of the core layers (P), (alkyl)alkoxysilane, catalyst for hydrolysis, water, and water-soluble organic solvent used in the reaction).

Use of water in an amount of 0.01 wt % or more relative to the weight of the (alkyl) alkoxysilane can reduce the reaction time for forming the shell layers (Q) having a desired average thickness, without excessively slowing down the reaction speed of hydrolysis of the (alkyl)alkoxysilane.

The water-soluble organic solvent may or may not be used. When used, each water-soluble organic solvent may be used alone or in combination of two or more thereof.

Examples of the water-soluble organic solvent include those exemplified in the description of step 1. Preferred examples are also the same as those described above.

In addition to the above, a nonionic surfactant or the like can also be used to improve the dispersibility of the core layers (P) during reaction.

Examples of the nonionic surfactant include those exemplified in the description of step 1. Preferred examples are also the same as those described above.

The temperature of the hydrolysis and polycondensation reaction of the (alkyl) alkoxysilane in step 2 is preferably 0° C. to 90° C., more preferably 15° C. to 50° C.

The reaction time of the hydrolysis and polycondensation reaction of the (alkyl)alkoxysilane in step 2 is preferably 1 to 5 hours, more preferably 1 to 3 hours.

The core-shell particles (C) in the present invention each include the shell layer (Q) that is a silica layer. Thus, a silanol group is present on the surface of each particle.

Therefore, the substance to be separated (D) of a predetermined type can be bonded to the surface.

As described above, the core-shell particles (C) allow binding of the substance to be separated (D) to the surfaces of the core-shell particles (C) via silanol groups of the core-shell particles (C).

A specific method is, for example, one in which the silanol groups of the core-shell particles (C) are bonded to the nucleotide chain of DNA that is the substance to be separated (D) via a chaotropic salt (e.g., guanidinium thiocyanate, guanidine hydrochloride, or sodium perchlorate) to form a complex (e.g., a reaction to form a complex via a chaotropic salt, disclosed in JP 2014-176393 A).

In the case where the substance to be separated (D) does not directly bind to the core-shell particles (C), a substance (G) that binds to the substance to be separated (D) may be immobilized on the surfaces of the core-shell particles (C). The immobilization of the substance (G) on the surfaces allows binding of the substance to be separated (D) to the core-shell particles (C) via the substance (G). Hereinafter, core-shell particles having surfaces with the substance (G) immobilized thereon are also referred to as "core-shell particles (C1)".

The substance to be separated (D) may be the target substance (D1) or the non-target substance (D2). The substance (G) may be any substance that binds to the target substance (D1) or the non-target substance (D2).

The binding between the substance (G) and the substance to be separated (D) may be specific or non-specific, but preferably, the binding between the substance (G) and the substance to be separated (D) is specific.

In the case where the binding between the substance to be separated (D) and the substance (G) is specific, the separation and purification method using the core-shell particles (C) of the present invention improves the separability of the substance to be separated (D).

Examples of the substance (G) that specifically binds to the substance to be separated (D) in the present invention include those that bind to the substance to be separated (D) by interactions such as "antigen"-"antibody" interaction, "glycan"-"protein" interaction, "glycan"-"lectin" interaction, "enzyme"-"inhibitor" interaction, "protein"-"peptide chain" interaction, "chromosome or nucleotide chain"-"nucleotide chain" interaction, and "nucleotide chain"-"protein" interaction.

In each of the interactions, when one is the substance to be separated (D), the other is the substance (G) that specifically binds to the substance to be separated (D).

For example, when the substance to be separated (D) is an "antigen", the substance (G) is an "antibody". When the substance to be separated (D) is an "antibody", the substance (G) is an "antigen".

The same shall apply to the other interactions.

The antibody used in the present invention also includes degradation products (e.g., Fab and F(ab')2 fragments) generated by proteolytic enzymes (e.g., papain and pepsin) and chemical decomposition.

In the present invention, examples of the method of immobilizing the substance (G) that specifically binds to the substance to be separated (D) on the core-shell particles (C) also include a method of physically adsorbing the substance (G) to the core-shell particles (C). In order to more efficiently immobilize the substance (G), at least one organic compound (K) selected from the group consisting of glutaraldehyde, a carbodiimide compound, streptavidin, biotin, and an alkylalkoxysilane (H) having a functional group may be bonded to the surfaces of the core-shell particles (C) to immobilize the substance (G) on the core-shell particles (C) via at least one organic compound (K).

More preferred of these organic compounds (K) is the alkylalkoxysilane (H) having a functional group, in terms of immobilization of a specific substance (G).

Examples of the functional group of the alkylalkoxysilane (H) include amino, carboxy, hydroxy, mercapto, and glycidyloxy groups. The alkylalkoxysilane may have different functional groups in one molecule.

Examples of the method of binding the alkylalkoxysilane (H) having a functional group to the surfaces of the core-shell particles (C) include a method in which an alkylalkoxysilane having an alkyl group substituted by an amino, carboxy, hydroxy, mercapto, or glycidyloxy group is used as the (alkyl)alkoxysilane in step 2 during production of the core-shell particles (C) by the method described above; and a method in which the core-shell particles (C) are prepared using an (alkyl)alkoxysilane having none of these substituents, and the core-shell particles (C) are subsequently treated with an alkylalkoxysilane having an alkyl group substituted by an amino, carboxy, hydroxy, mercapto, or glycidyloxy group.

One of specific examples of the latter method is one in which the core-shell particles (C) are dispersed in a solvent to give a concentration of 0.1 to 50 wt % relative to the weight of the solvent; and a solution of an alkylalkoxysilane having an alkyl group substituted by an amino, carboxy, hydroxy, mercapto, or glycidyloxy group is added to the dispersion for hydrolysis and condensation at room temperature.

The solvent in this method is appropriately selected depending on the solubility of an alkylalkoxysilane to be used. For example, water or a water-alcohol mixed solvent is preferred for a water-soluble alkylalkoxysilane having an alkyl group substituted by an amino, carboxy, hydroxy, or mercapto group. Butyl acetate is preferred for a slightly water-soluble alkylalkoxysilane having an alkyl group substituted by a glycidyloxy group.

The amount of the alkylalkoxysilane having an alkyl group substituted by an amino, carboxy, hydroxy, mercapto, or glycidyloxy group is preferably 0.0001 to 100 wt %, based on the weight of the core-shell particles (C) before the substance (G) is immobilized thereon.

An amount of 0.0001 wt % or more allows introduction of a sufficient number of functional groups into the surfaces of the core-shell particles (C). An amount of 100 wt % or less can inhibit the core-shell particles (C) from reacting with each other and binding to each other.

Glutaraldehyde, a carbodiimide compound, streptavidin, or biotin may be bonded to the surfaces of the core-shell particles (C) by any method. An example method is as follows.

Glutaraldehyde having an aldehyde group and biotin having a carboxy group can be bonded to the surfaces of the core-shell particles (C) by reaction with the core-shell particles (C) each having a surface to which an alkylalkoxysilane having an amino-substituted alkyl group is bonded.

Streptavidin having an amino group and a carbodiimide compound having a carbodiimide group can be bonded to the surfaces of the core-shell particles (C) by reaction with the core-shell particles (C) each having a surface to which an alkylalkoxysilane having a carboxy-substituted alkyl group is bonded.

The substance (G) is immobilized on the core-shell particles (C) via the organic compound (K) by appropriately selecting the organic compound (K) depending on the type of the substance (G).

For example, the substance (G) having a streptavidin structure can be immobilized by a known method by selecting biotin as the organic compound (K).

The substance (G) having a biotin structure can be immobilized by a known method by selecting streptavidin as the organic compound (K).

The substance (G) having an amino group can be immobilized by a known method by selecting glutaraldehyde as the organic compound (K).

The substance (G) having a carboxy group can be immobilized by a known method by selecting a carbodiimide compound as the organic compound (K).

When the organic compound (K) is the alkylalkoxysilane (H) having a functional group, the following substance (G) can be bonded depending on the functional group of the alkylalkoxysilane (H).

For example, when the functional group of the alkylalkoxysilane (H) is an amino group, the substance (G) having a carboxy group, a carbonyl group, and/or an aldehyde group can be immobilized by a known method.

When the functional group of the alkylalkoxysilane (H) is a carboxy group, the substance (G) having an amino group can be immobilized by a known method.

When the functional group of the alkylalkoxysilane (H) is a hydroxy group, the substance (G) having a carboxy group can be immobilized by a known method.

When the functional group of the alkylalkoxysilane (H) is a mercapto group, the substance (G) having a mercapto group can be immobilized by a known method.

When the functional group of the alkylalkoxysilane (H) is a glycidyloxy group, the substance (G) having an amino group and/or hydroxy group can be immobilized by a known method.

Alternatively, the substance (G) may be immobilized on the core-shell particles (C) via a reaction product of another compound with the organic compound (K).

For example, when the organic compound (K) is an alkylalkoxysilane having an amino group, the organic compound (K) may be reacted with succinic anhydride to produce a carboxy group. In this case, the substance (G) having an amino group can be immobilized by a known method.

Examples of the method include one using 1-ethyl-3-(3-dimethylaminopropyl)carbodiimide hydrochloride (EDC) and N-hydroxysuccinimide (NHS).

Examples of the substance (G) that non-specifically binds to the substance to be separated (D) in the present invention include those having a functional group (J) that binds to the substance to be separated (D) by a covalent bond, a hydrogen bond, a hydrophobic interaction, an ionic bond, or the like.

Preferably, the functional group (J) is an amino group, an ammonium group, or the like because these functional groups can quickly form strong bonds in an aqueous solution.

Examples of the amino group include primary, secondary, and tertiary amino groups. Examples of the ammonium group include salts of the primary, secondary, and tertiary amino groups with acids (e.g., hydrochloric acid, oxalic acid, folic acid, acetic acid, sulfuric acid, nitric acid, and phosphoric acid) and quaternary ammonium groups.

Here, examples of the group having a primary amino group include aminoalkyl groups such as amino, aminomethyl, aminoethyl, and aminopropyl groups, and aminoalkoxyalkyl groups such as 3-amino-1-ethoxypropyl and 1-amino-ethoxymethyl groups.

Examples of the secondary amino group include amino groups in which a single hydrogen atom is replaced by a hydrocarbon group. Examples of the group having a secondary amino group include N-alkylaminoalkyl groups such as N-methylaminoethyl and N-ethylaminoethyl groups, and an imidazolyl group.

Examples of the tertiary amino group include amino groups in which two hydrogen atoms are replaced by hydrocarbon groups. Examples of a functional group having a tertiary amino group include N-dimethylaminoethyl, N-dimethylaminopropyl, N-diethylaminoethyl, and N-dibutyl aminoethyl groups.

Examples of the quaternary ammonium groups include ammonium groups in which three hydrogen atoms are replaced by hydrocarbon groups. Examples of functional groups having a quaternary ammonium group include trialkylammonium groups such as trimethylammonium and triethylammonium groups.

Components as counter ions of the quaternary ammonium groups may be a hydroxide ion, an acid-derived anion, and the like. Examples of the acid include hydrochloric acid, oxalic acid, folic acid, acetic acid, sulfuric acid, nitric acid, and phosphoric acid.

Examples of the method of immobilizing the substance (G) containing an amino group or an ammonium group on the core-shell particles (C) include a method in which an alkylalkoxysilane having an amino-substituted alkyl group is used as the (alkyl)alkoxysilane in step 2 during production of the core-shell particles (C) by the method described above; and a method described in detail below in which the core-shell particles (C) are reacted with a compound having an amino group or an ammonium group.

Specifically, the core-shell particles (C) are reacted with a compound having a primary, secondary, or tertiary amino group or a quaternary ammonium group by the following method.

Examples of the method of reacting the core-shell particles (C) with a compound having a primary amino group include a method of reacting alkylene diamine with the hydroxy group and/or carboxy group of each core-shell particle (C).

The hydroxy group of each core-shell particle (C) refers to a group derived from the silanol group of the shell layer (Q) or a group derived from the alkylalkoxysilane having a hydroxy group.

The carboxy group of each core-shell particle (C) is a group derived from an alkylalkoxysilane having a carboxy group.

Specifically, the carboxy group is reacted with a carbodiimide compound in advance to obtain acylisourea (R'—N=C(OCOR)—NH—R' (—OCOR is a site derived from the core-shell particles (C) having a carboxy group)), and alkylene diamine is subsequently added to the acylisourea, whereby a compound having a primary amino group can be amide-bonded to the core-shell particles (C).

The amount of the compound having a primary amino group bonded is preferably 0.01 to 10 mmol/g based on the weight of the core-shell particles (C) before the substance (G) is immobilized thereon, in terms of separability of the substance to be separated (D).

Examples of the method of reacting the core-shell particles (C) with a compound having a secondary amino group include a method of reaching N-alkylaminoalkylamine with the hydroxy group and/or carboxy group of each core-shell particle (C).

Specifically, the carboxy group is reacted with a carbodiimide compound in advance to obtain acylisourea (R'—N=C(OCOR)—NH—R' (—OCOR is a site derived from the core-shell particles (C) having a carboxy group)), and N-alkylaminoalkylamine is subsequently added to the acylisourea, whereby a compound having a secondary amino group can be amide-bonded to the core-shell particles (C). The amount of the compound having a secondary amino group bonded is preferably 0.01 to 10 mmol/g based on the weight of the core-shell particles (C) before the substance (G) is immobilized thereon, in terms of separability of the substance to be separated (D).

Examples of the method of reacting the core-shell particles (C) with a compound having a tertiary amino group include a method of reacting N-dialkylaminoalkylchloride with the hydroxy group and/or carboxy group of each core-shell particle (C).

Specifically, an ester bond is formed with the carboxy group of each core-shell particle (C) or an ether bond is formed with the hydroxy group of each core-shell particles (C) by reaction in an aqueous solution in the presence of NaOH (sodium hydroxide).

Examples of the method of reacting the core-shell particles (C) with a compound having a quaternary ammonium group include a method of reacting N-glycidil-trialkylammoniumchloride with the carboxy group and/or hydroxy group of each core-shell particle (C).

Specifically, an ester bond is formed with the carboxy group of each core-shell particle (C) or an ether bond is formed with the hydroxy group of each core-shell particle (C) by reaction in an aqueous solution in the presence of a quaternary ammonium salt catalyst.

Next, the separation and purification method of separating the substance to be separated (D) from the sample (E) using the core-shell particles (C) of the present invention is described below with two examples.

These separation and purification methods are encompassed by the separation and purification method of the present invention.

(First Separation and Purification Method)

The first separation and purification method is a method in which the substance to be separated (D) is the target substance (D1), and the target substance (D1) is extracted and purified from a sample (E1) containing the target substance (D1).

The first separation and purification method includes (1) a composite formation step, (2) a composite separation step, and (3) a target substance dissociation step.

Each step is described below.

(1) Composite Formation Step

In this step, the sample (E1) containing the target substance (D1) is contacted with the core-shell particles (C) to form a composite (F1) of the core-shell particles (C) and the target substance (D1).

The composite (F1) may be formed by direct binding of the target substance (D1) to the core-shell particles (C).

Alternatively, the core-shell particles (C) may contain the substance (G) that binds to the target substance (D1), and the composite (F1) may be formed by binding of the target substance (D1) to the core-shell particles (C) via the substance (G).

(2) Composite Separation Step

Next, the composite (F1) is separated from the sample (E1) by a magnetic force.

The composite (F1) contains the core-shell particles (C), and the core-shell particles (C) contain the magnetic metal oxide particles (A), so that the composite (F1) can be collected by a magnetic force.

Subsequently, the remaining sample (E1) is removed, whereby the sample (E1) can be separated from the composite (F1).

Examples of such a method include one in which the composite (F1) is collected by a magnetic force of a magnet or the like from the outside of a reaction vessel; the supernatant (a sample (E11) with the target substance (D1) removed therefrom) is discharged; and the composite (F1) is separated.

The separated composite (F1) may be washed with a washing solution in order to remove contaminants attached to the composite (F1). The washing operation may be repeated 1 to 10 times.

The washing solution may be a physiological saline solution, a phosphate buffer solution, or the like.

The washing solution may contain a surfactant. The surfactant is preferably a nonionic surfactant.

Examples of the nonionic surfactant include adducts of alkylene oxide (hereinafter, alkylene oxide is abbreviated to "AO") with C8-C24 monohydric alcohols (e.g., decyl alcohol, dodecyl alcohol, coconut oil alkyl alcohol, octadecyl alcohol, and oleyl alcohol);

adducts of AO with C3-C36 dihydric to octahydric alcohols (e.g., glycerol, trimethylolpropane, pentaerythritol, sorbitol, and sorbitan);
   adducts of AO with alkylphenols having C6-C24 alkyl (e.g., octylphenol and nonylphenol);
   adducts of ethylene oxide with polypropylene glycol, and adducts of propylene oxide with polyethylene glycol;
   adducts of AO with C8-C24 fatty acids (e.g., decanoic acid, lauric acid, myristic acid, palmitic acid, stearic acid, oleic acid, and coconut oil fatty acid);
   fatty acid esters of the C3-C36 dihydric to octahydric alcohols and AO adducts thereof (e.g., TWEEN® 20 and TWEEN® 80);
   alkyl glucosides (e.g., N-octyl-β-D-maltoside, n-dodecanoylsucrose, and n-octyl-β-D-glucopyranoside); and
   fatty acid esters of sucrose, fatty acid alkanolamide, and AO adducts thereof (e.g., polyoxyethylene fatty acid alkanolamide).

Each of these may be used alone or in combination of two or more thereof.

Examples of the AO in the description of the nonionic surfactant include ethylene oxide, propylene oxide, and butylene oxide. The AO may be added in the form of either block or random.

The number of moles of AO added is preferably 1 to 50 moles, more preferably 1 to 20 moles, per mole of alcohol, phenol, or fatty acid.

In terms of solubility in water and viscosity, preferred of these nonionic surfactants are adducts of 1 to 50 mol (preferably 1 to 20 mol) ethylene oxide with a C8-C24 monohydric alcohol, such as polyoxyethylene alkyl ether and polyoxyethylene alkenyl ether.

Preferably, the operation to separate the composite (F1) from the sample (E1) is repeated 1 to 10 times. Repetition of this operation allows separation of a large amount of the composite (F1) from the sample (E1).

(3) Target Substance Dissociation Step

Next, the target substance (D1) is dissociated from the composite (F1) to obtain the target substance (D1).

The target substance (D1) may be dissociated from the composite (F1) by any method, such as one in which a substance that inhibits binding between the core-shell particles (C) and the target substance (D1) is added to dissociate the target substance (D1).

The substance that inhibits binding between the core-shell particles (C) and the target substance (D1) varies depending on the types of the target substance (D1) and the substance (G), but the examples thereof include those that inhibit binding by the pH difference, salinity difference, or action of a surfactant. Examples of the surfactant capable of inhibiting binding include lauryl sulfate and dodecylbenzene sulfonate.

When the composite (F1) is a complex of the core-shell particles (C) and the target substance (D1) via the chaotropic salt, concentrated Tris-EDTA buffer or the like can be used as a substance that inhibits binding between the core-shell particles (C) and the target substance (D1).

Preferably, the Tris-EDTA buffer is one containing 50 mM or more tris(hydroxymethyl)aminomethane and 10 mM or more tetrasodium ethylenediaminetetraacetate.

The target substance (D1) can be separated and purified by the above steps.

When the target substance (D1) is obtained by the above method, since the target substance (D1) can be selectively bonded to the core-shell particles (C) in the composite formation step (due to the excellent separability of the substance to be separated (D)), it is possible to increase the purity of the target substance (D1) in the resulting separated and purified product.

The first separation and purification method may include a core-shell particle retrieving step of retrieving the core-shell particles (C) after the target substance dissociation step (3).

In the target substance dissociation step (3), the core-shell particles (C) and the target substance (D1) are dissociated from each other.

These core-shell particles (C) can be retrieved and reused.

Thus, after the core-shell particle retrieving step, the composite formation step (1), the composite separation step (2), and the target substance dissociation step (3) may be repeated using the retrieved core-shell particles (C).

In reuse of the core-shell particles (C), the sample (E1) to be contacted again may be the sample (E11) containing the residual target substance (D1).

Reuse of the core-shell particles (C) can reduce the cost for separation and purification of the target substance (D1).

(Second Separation and Purification Method)

The second separation and purification method is a method in which the substance to be separated (D) is the non-target substance (D2), and the non-target substance (D2) is removed from a sample (E2) containing the target substance (D1) and the non-target substance (D2) so as to purify the target substance (D1).

The second separation and purification method includes (1) a composite formation step and (2) a non-target substance removal step.

Each step is described below.

(1) Composite Formation Step

In this step, the sample (E2) containing the target substance (D1) and the non-target substance (D2) is contacted with the core-shell particles (C) to form a composite (F2) of the core-shell particles (C) and the non-target substance (D2).

The composite (F2) may be formed by direct binding of the non-target substance (D2) to the core-shell particles (C).

Alternatively, the core-shell particles (C) may contain the substance (G) that binds to the non-target substance (D2), and the composite (F2) may be formed by binding of the non-target substance (D2) to the core-shell particles (C) via the substance (G).

(2) Non-Target Substance Removal Step

Next, the composite (F2) is separated from the sample (E2) by a magnetic force, whereby the non-target substance (D2) is removed from the sample (E2), and a sample (E21) containing the target substance (D1) is obtained.

The composite (F2) contains the core-shell particles (C), and the core-shell particles (C) contain the magnetic metal oxide particles (A), so that the composite (F2) can be collected by a magnetic force.

Subsequently, the remaining sample (E21) is collected, whereby the sample (E21) can be separated from the composite (F2).

Examples of such a method include one in which the composite (F2) is collected by a magnetic force of a magnet or the like from the outside of a reaction vessel; the supernatant is collected; and the sample (E21) is separated.

When the non-target substance (D2) has not been sufficiently removed from the sample (E21), the composite formation step (1) and the non-target substance removal step (2) may be repeated using the sample (E21), whereby the non-target substance (D2) is further removed from the sample (E21).

In the second separation and purification method, the non-target substance (D2) includes multiple types of non-target substances, and the sample (E2) may contain the multiple types of non-target substances (D2).

In this case, the multiple non-target substances (D2) can be removed from the sample (E2) using a single or multiple types of core-shell particles (C) capable of binding to the multiple non-target substances (D2), respectively.

The sample (E21) containing the target substance (D1) can be separated and purified by the above steps.

The target substance (D1) can be further obtained from the sample (E21) by a known method such as filtration or distillation.

When the target substance (D1) is obtained by the above method, the non-target substance (D2) can be selectively bonded to the core-shell particles (C) in the composite formation step, so that the non-target substance (D2) is present in a lower proportion in a component with the non-target substance (D2) removed therefrom. As a result, it is possible to increase the proportion of the target substance (D1) in the sample (E21).

The second separation and purification method may include a core-shell particle retrieving step of retrieving the core-shell particles (C) from the composite (F2) after the non-target substance removal step.

The core-shell particles (C) may be retrieved from the composite (F2) by any method, such as one in which a substance that inhibits binding between the core-shell particles (C) and the non-target substance (D2) is added to dissociate the core-shell particles (C).

The substance that inhibits binding between the core-shell particles (C) and the non-target substance (D2) varies depending on the types of the non-target substance (D2) and the substance (G), but the examples thereof include those that inhibit binding by the pH difference, salinity difference, or action of a surfactant. Examples of the surfactant capable of inhibiting binding include lauryl sulfate and dodecylbenzene sulfonate.

When the composite (F2) is a complex of the core-shell particles (C) and the non-target substance (D2) via the chaotropic salt, concentrated Tris-EDTA buffer or the like can be used as a substance that inhibits binding between the core-shell particles (C) and the non-target substance (D2).

Preferably, the Tris-EDTA buffer is one containing 50 mM or more tris(hydroxymethyl)aminomethane and 10 mM or more tetrasodium ethylenediaminetetraacetate.

These core-shell particles (C) can be retrieved and reused.

Thus, after the core-shell particle retrieving step, the composite formation step (1) and the non-target substance removal step (2) may be repeated using the retrieved core-shell particles (C).

In reuse of the core-shell particles (C), the sample (E2) to be contacted again may be the sample (E21) containing the residual non-target substance (D2).

Reuse of the core-shell particles (C) can reduce the cost for separation and purification of the target substance (D1).

Examples of the target substance (D1) in the separation and purification method of the present invention include
proteins (e.g., albumin, hemoglobin, myoglobin, transferrin, protein A, C-reactive protein (CRP), lipoproteins, enzymes, immunoglobulins, immunoglobulin fragments, blood coagulation related factors, antibodies, antigens, and hormones),
nucleic acids (e.g., deoxyribonucleic acid (DNA) and ribonucleic acid (RNA)),
drugs (e.g., anticonvulsants, antibiotics, and theophylline),
viruses (e.g., hepatitis C virus, hepatitis B virus, hepadnavirus, adenovirus, rhabdovirus, flavivirus, retrovirus, herpesvirus, and orthomyxovirus),
bacteria (e.g., 0-157, *Helicobacter pylori*, and *Salmonella*),
cells (e.g., fat cells, ES cells, hepatocytes, stem cells, endothelial cells, epithelial cells, muscle cells, endocrine cells, exocrine cells, nerve cells, tumor cells, and IPS cells).

Examples of the enzyme include alkaline phosphatase, amylase, acid phosphatase, γ-glutamyl transferase (γ-GTP), lipase, creatine kinase (CK), lactate dehydrogenase (LDH), glutamic oxaloacetic transaminase (GOT), glutamic-pyruvic transaminase (GPT), renin, protein kinase (PK), and tyrosine kinase.

Examples of the lipoprotein include high-density lipoproteins (HDL), low-density lipoproteins (LDL), and very-low-density lipoproteins.

Examples of the immunoglobulin include IgG, IgM, IgA, IgD, and IgE.

Examples of the immunoglobulin fragment include Fc, Fab, and F(ab')$_2$ fragments.

Examples of the blood coagulation related factor include fibrinogen/fibrin degradation products (FDP), prothrombin, and thrombin.

Examples of the antibody include anti-streptolysin O antibody, anti-Hepatitis B surface antigen (HBs antigen) antibody, anti-Hepatitis C antibody, and anti-rheumatoid factor.

Examples of the antigen include carcinoembryonic antigen (CEA).

Examples of the hormone include thyroid stimulating hormone (TSH), thyroid hormone (FT3, FT4, T3, T4), parathyroid hormone (PTH), human chorionic gonadotropin (hCG), and estradiol (E2).

Examples of the antigen and the antibody also include substances known as cancer markers (e.g., α-fetoprotein (AFP), carcinoembryonic antigen (CEA), CA19-9, and prostate-specific antigen (PSA)) and cardiac markers (e.g., troponin T (TnT) and N-terminal fragment of brain natriuretic peptide precursor (NT-proBNP)).

Preferred of these are nucleic acids, antigens, antibodies, and hormones.

The non-target substance (D2) in the present invention refers to at least one substance in the sample (E), with the target substance (D1) removed therefrom. In other words, the non-target substance (D2) may include multiple types of non-target substances (D2).

For example, when the sample (E) is serum, and carcinoembryonic antigen (CEA) in the serum is the target substance (D1), at least one of other components in the serum, such as proteins (e.g., albumin, antibodies, and antigens other than CEA), lipids, and inorganic matter, is the non-target substance (D2).

In the present invention, preferably, the substance to be separated (D) is at least one selected from the group consisting of a DNA, an RNA, a cell, a virus, a bacterium, and a protein.

EXAMPLES

The present invention is further described below with reference to examples, but the present invention is not limited to these examples. Hereinafter, "%" indicates "wt %", and "part(s)" indicates "part(s) by weight", unless otherwise specified.

Production Example 1: Production of Core-Shell Particles (C1-1)

<Production of the Magnetic Metal Oxide Particles (A)>

A reaction vessel was charged with iron(III) chloride hexahydrate (186 parts), iron(II) chloride tetrahydrate (68 parts), and water (1288 parts). These components were dissolved, and the solution was heated to 50° C., and 25 wt % ammonia water (280 parts) was added dropwise over one hour while the temperature was maintained at 50° C. to 55° C. under stirring. Thus, magnetite particles were obtained in the water. Oleic acid (64 parts) as a dispersant was added to the resulting magnetite particles, and stirring was continued for two hours. After cooling to room temperature, the mixture was subjected to solid-liquid separation by decantation to obtain magnetite particles on which oleic acid had been adsorbed, which were then washed with water (1000 parts) three times and then washed with acetone (1000 parts) twice, followed by drying at 40° C. for two days. Thus, magnetic metal oxide particles (A-1) having a volume average particle size of 15 nm were obtained.

<Production of Core Layers (P)>

The magnetic metal oxide particles (A) (80 parts) were added and dispersed in tetraethoxysilane (240 parts) to prepare a dispersion (B1). Next, a reaction vessel was charged with water (5050 parts), a 25 wt % ammonia aqueous solution (3500 parts), and Emalmin 200 (Sanyo Chemical Industries, Ltd.) (400 parts), and these components were mixed using Clearmix (M Technique Co., Ltd.) to obtain a solution (B2). After heating to 50° C., the dispersion (B1) was added dropwise to the solution (B2) over one hour under stirring with Clearmix at a rotation speed of 6000 rpm, followed by reaction at 50° C. for one hour. After the reaction, the supernatant containing fine particles was removed by centrifugation at 2000 rpm for 20 minutes. Thus, core layers (P-1) each containing the magnetic metal oxide particles (A-1) in an amount of 83 wt % were obtained.

<Production of Core-Shell Particles (PC)>

A reaction vessel was charged with the core layers (P-1) (80 parts), deionized water (2500 parts), a 25 wt % ammonia aqueous solution (260 parts), ethanol (2500 parts), and tetraethoxysilane (1200 parts), and these components were mixed using Clearmix (M Technique). The mixture was reacted for two hours under stirring with Clearmix at a rotation speed of 6000 rpm. After the reaction, the supernatant containing fine particles was removed by centrifugation at 2000 rpm for 20 minutes. Deionized water (4000 parts) was added to the precipitated particles after centrifugation to re-disperse the particles. The dispersed particles were magnetically collected by contact with a magnet from the outside of the vessel, and the supernatant was removed. This operation was repeated 10 times. Thus, core-shell particles (PC-1) were obtained.

<Classification Step of Core-Shell Particles (PC)>

Water (5000 parts) was added to a solid phase containing the resulting core-shell particles (PC-1) to disperse the particles. The dispersion was centrifuged at 2800 rpm for one minute, and then the supernatant containing fine particles was removed. This operation was repeated four times (centrifugation step 1).

Subsequently, water (5000 parts) was added to the resulting solid phase to disperse the particles, followed by centrifugation at 600 rpm for one minute to collect the supernatant, whereby large-sized precipitated particles were removed. This operation was performed once (centrifugation step 2).

Further, the particles were magnetically collected using a magnet, and the supernatant was removed. Subsequently, after water (5000 parts) was added to disperse the core-shell particles, the particles were magnetically collected using a magnet, and the supernatant was removed. This operation was repeated 10 times (washing step 1). Thus, core-shell particles (C-1) were obtained.

<Production of Core-Shell Particles (C1) Carrying Anti-AFP Antibodies>

The core-shell particles (C-1) (50 mg) after classification were added to a lidded polyethylene bottle containing an aqueous solution (400 mL) containing 1 wt % γ-aminopropyltriethoxysilane, followed by reaction at 25° C. for one hour. After magnetically collecting the particles with a magnet, the solution was removed by suction using an aspirator. Then, deionized water (400 mL) was added to disperse the core-shell particles, and the particles were magnetically collected with a magnet, followed by removal of the solution by suction using an aspirator to wash the core-shell particles. This washing operation was repeated four times.

Then, the core-shell particles after washing were added to a lidded polyethylene bottle containing an ethanol solution (100 mL) containing 0.5 wt % succinic anhydride, followed by reaction at 25° C. for two hours. After magnetically collecting the particles with a magnet, the solution was removed by suction using an aspirator. Then, deionized water (400 mL) was added to disperse the core-shell particles, and the particles were magnetically collected with a magnet, followed by removal of the solution by suction using an aspirator to wash the core-shell particles. This washing operation was repeated three times.

Then, the core-shell particles after washing was added to a lidded polyethylene bottle containing an aqueous solution (400 mL) containing 0.5 wt % 1-ethyl-3-(3-dimethylaminopropyl)carbodiimide hydrochloride (EDC) and 0.5 wt % N-hydroxysuccinimide (NHS), followed by reaction at 25°

C. for one hour. After magnetically collecting the particles with a magnet, the solution was removed by suction using an aspirator.

Then, after 25 mM morpholine ethane sulfonic acid buffer (pH 5.0) (200 mL) was added to re-disperse the particles, the particles were magnetically collected again with a magnet, and the solution was removed by suction using an aspirator to wash the core-shell particles. This washing operation was repeated three times.

Further, the core-shell particles after washing were added to a lidded polyethylene bottle containing 100 mM morpholine ethane sulfonic acid buffer (pH 5.0) (400 mL) containing an anti-AFP polyclonal antibody (purchased from Dako-Cytomation Co., Ltd.) at a concentration of 20 µg/mL, followed by reaction at 25° C. for three hours. After the reaction, the particles were magnetically collected with a magnet, and the solution was removed by suction using an aspirator.

Then, after 25 mM morpholine ethane sulfonic acid buffer (pH 5.0) (200 mL) was added to re-disperse the particles, the particles were magnetically collected again with a magnet, and the solution was removed by suction using an aspirator to wash the core-shell particles. This washing operation was repeated three times. Thus, core-shell particles (C1-1) were obtained. These particles were immersed in a 0.02 M phosphate buffer (pH 7.2) (50 mL) containing 0.1 wt % Blockmaster CE510 (JSR) and stored at 4° C.

Production Examples 2 to 4, Production Examples 9 to 11, and Production Examples 15 to 16: Production of Core-Shell Particles (C1-2) to (C1-4), (C1-9) to (C1-11), and (C1-15) to (C1-16)

The same operation as in Production Example 1 was carried out, except that the conditions for <Classification step of core-shell particles (PC)> of Production Example 1 were changed as described in Table 1, whereby core-shell particles (C1-2) to (C1-4), (C1-9) to (C1-11), and (C1-15) to (C1-16) were obtained.

Production Example 5: Production of Core-Shell Particles (C1-5)

The same operation as in Production Example 1 was carried out, except that the amount of tetraethoxysilane was changed from 1200 parts to 15 parts in "Production of core-shell particles (PC)" of Production Example 1 and that the conditions for "Classification step of core-shell particles (PC)" of Production Example 1 were changed as described in Table 1, whereby core-shell particles (C1-5) were obtained.

Production Example 6: Production of Core-Shell Particles (C1-6)

The same operation as in Production Example 1 was carried out, except that the amount of tetraethoxysilane was changed from 1200 parts to 150 parts in "Production of core-shell particles (PC)" of Production Example 1 and that the conditions for "Classification step of core-shell particles (PC)" of Production Example 1 were changed as described in Table 1, whereby core-shell particles (C1-6) were obtained.

Production Example 7: Production of Core-Shell Particles (C1-7)

The same operation as in Production Example 1 was carried out, except that the amount of tetraethoxysilane was changed from 1200 parts to 3000 parts in "Production of core-shell particles (PC)" of Production Example 1 and that the conditions for "Classification step of core-shell particles (PC)" of Production Example 1 were changed as described in Table 1, whereby core-shell particles (C1-7) were obtained.

Production Example 8: Production of Core-Shell Particles (C1-8)

The same operation as in Production Example 1 was carried out, except that the amount of tetraethoxysilane was changed from 1200 parts to 10000 parts in "Production of core-shell particles (PC)" of Production Example 1 and that the conditions for "Classification step of core-shell particles (PC)" of Production Example 1 were changed as described in Table 1, whereby core-shell particles (C1-8) were obtained.

Production Example 12: Production of Core-Shell Particles (C1-12)

The same operation as in Production Example 2 was carried out, except that the amount of the magnetic metal oxide particles (A) was changed from 80 parts to 60 parts in "Production of core layers (P)" of Production Example 2, whereby core-shell particles (C1-12) were obtained.

Production Example 13: Production of Core-Shell Particles (C1-13)

The same operation as in Production Example 2 was carried out, except that the amount of the magnetic metal oxide particles (A) was changed from 80 parts to 100 parts in "Production of core layers (P)" of Production Example 2, whereby core-shell particles (C1-13) were obtained.

Production Example 14: Production of Core-Shell Particles (C1-14)

The same operation as in Production Example 2 was carried out, except that the amount of tetraethoxysilane was changed from 1200 parts to 600 parts in "Production of core-shell particles (PC)" of Production Example 2, whereby core-shell particles (C1-14) were obtained.

Comparative Production Example 1: Production of Comparative Particles (C1'-1)

The same operation as in Production Example 1 was carried out, except that NSA-17 (Sanyo Chemical Industries, Ltd.) was used instead of Emalmin 200 in "Production of core layers (P)" of Production Example 1 and that the conditions for <Classification step of core-shell particles (PC)> of Production Example 1 were changed as described in Table 1, whereby comparative particles (C1'-1) were obtained.

Comparative Production Example 2: Production of Comparative Particles (C1'-2)

The same operation as in Production Example 1 was carried out, except that NSA-17 (Sanyo Chemical Industries, Ltd.) was used instead of Emalmin 200 in "Production of core layers (P)" of Production Example 1 and that the conditions for <Classification step of core-shell particles (PC)> of Production Example 1 were changed as described in Table 1, whereby comparative particles (C1'-2) were obtained.

Comparative Production Example 3: Production of Comparative Particles (C1'-3)

The following operation was carried out using the core layers (P-1) obtained in Production Example 1 as the comparative particles (PC'-1).
<Classification Step of Core-Shell Particles (PC')>
Water (5000 parts) was added to the whole amount of the magnetic silica particles (particles (PC'-1)) obtained in "Production of core layers (P)" of Production Example 1 to disperse the particles. The dispersion was centrifuged at 1600 rpm for one minute, and then the supernatant containing fine particles was removed. This operation was repeated 20 times (centrifugation step 1).

Subsequently, water (5000 parts) was added to the resulting solid phase to disperse the particles, followed by centrifugation at 800 rpm for one minute, whereby large-sized particles were precipitated and removed. This operation was performed once (centrifugation step 2).

Further, the particles were magnetically collected with a magnet, and the supernatant was removed. Subsequently, after water (5000 parts) was added to disperse the particles, the particles were magnetically collected with a magnet, and the supernatant was removed. This operation was repeated 10 times (washing step 1). Thus, particles (C'-3) were obtained.
<Production of Particles (C1') Carrying Anti-AFP Antibodies>
The particles (C'-3) (50 mg) after classification were added to a lidded polyethylene bottle containing an aqueous solution (400 mL) containing 1 wt % γ-aminopropyltriethoxysilane, followed by reaction at 25° C. for one hour. After magnetically collecting the particles with a magnet, the solution was removed by suction using an aspirator. Then, deionized water (400 mL) was added to disperse the particles, and the particles were magnetically collected with a magnet, followed by removal of the solution by suction using an aspirator to wash the particles. This washing operation was repeated four times.

Then, the particles after washing were added to a lidded polyethylene bottle containing an ethanol solution (100 mL) containing 0.5 wt % succinic anhydride, followed by reaction at 25° C. for two hours. After magnetically collecting the particles with a magnet, the solution was removed by suction using an aspirator. Then, deionized water (400 mL) was added to disperse the particles, and the particles were magnetically collected with a magnet, followed by removal of the solution by suction using an aspirator to wash the particles. This washing operation was repeated three times.

Then, the particles after washing were added to a lidded polyethylene bottle containing an aqueous solution (400 mL) containing 0.5 wt % 1-ethyl-3-(3-dimethylaminopropyl)carbodiimide hydrochloride (EDC) and 0.5 wt % N-hydroxysuccinimide (NHS), followed by reaction at 25° C. for one hour. After magnetically collecting the particles with a magnet, the solution was removed by suction using an aspirator.

Then, after 25 mM morpholine ethane sulfonic acid buffer (pH 5.0) (200 mL) was added to re-disperse the particles, the particles were magnetically collected again with a magnet, and the solution was removed by suction using an aspirator to wash the particles. This washing operation was repeated three times.

Further, the particles after washing were added to a lidded polyethylene bottle containing 100 mM morpholine ethane sulfonic acid buffer (pH 5.0) (400 mL) containing an anti-AFP polyclonal antibody (purchased from DakoCytomation Co., Ltd.) at a concentration of 20 μg/mL, followed by reaction at 25° C. for three hours. After the reaction, the particles were magnetically collected with a magnet, and the solution was removed by suction using an aspirator.

Then, after 25 mM morpholine ethane sulfonic acid buffer (pH 5.0) (200 mL) was added to re-disperse the particles, the particles were magnetically collected again with a magnet, and the solution was removed by suction using an aspirator to wash the particles. This washing operation was repeated three times, whereby comparative particles (C1'-3) were obtained. These particles were immersed in a 0.02 M phosphate buffer (pH 7.2) (50 mL) containing 0.1 wt % Blockmaster CE510 (JSR) and stored at 4° C.

Comparative Production Example 4: Production of Comparative Particles (C1'-4)

The same operation as in Comparative Production Example 1 was carried out, except that the conditions for <Classification step of core-shell particles (PC')> of Comparative Production Example 4 were changed as described in Table 1, whereby particles (C1'-4) were obtained.

The magnetic metal oxide particles (A-1), the core-shell particles (C1-1) to (C1-16), and the comparative particles (C1'-1) to (C1'-4) obtained in Production Examples 1 to 16 and Comparative Production Examples 1 to 4 were evaluated as follows.
<Method of Measuring Volume Average Particle Size of Magnetic Metal Oxide Particles (A)>
Any 200 magnetic metal oxide particles (A) were observed using a scanning electron microscope (model number: JSM-7000F, manufacturer name: JEOL Ltd.) to measure the particle size, and the volume average particle size was determined. Table 1 shows the results.
<Method of Measuring Weight Percentage of Magnetic Metal Oxide Particles (A)>
Any 20 core layers (P) obtained in "Production of core layers (P)" of Production Example 1 were observed using a scanning electron microscope (model number: JSM-7000F, manufacturer name: JEOL Ltd.), and the amount of the magnetic metal oxide particles (A) was measured using an energy dispersive X-ray spectrometer (model number: INCA Wave/Energy; manufacturer name: Oxford Instruments). The average thereof was regarded as the amount S. The amount of silica was also measured by the same measurement, and the average thereof was regarded as the amount T. The weight percentage of the magnetic metal oxide particles (A) was determined by the following calculation formula. Table 1 shows the results.

Weight percent (wt %) of magnetic metal oxide particles $(A)=[(S)/(S+T)]\times 100$ <Method of Measuring Volume Average Particle Size Core-Shell Particles (C1) and Coefficient of Variation of Particle Size>
The volume average particle size and the coefficient of variation of the particle size of the core-shell particles (C1-1) to (C1-16) and the comparative particles (C1'-1) to (C1'-4) were measured using phosphate buffer solutions containing the core-shell particles obtained in the production examples as samples, by a laser diffraction/scattering particle size distribution measuring device ("Microtrac MT3300" from MicrotracBEL Corp.). Table 1 shows the results.

<Method of Measuring Average Thickness of Shell Layers (Q)>

The core-shell particles (C) obtained by the classification step of the core-shell particles (PC) or the comparative particles (C') obtained by the classification step of the particles (PC') were embedded in an epoxy resin, and microtome cross sections of the particles were observed by a transmission electron microscope (model number "H-7100", Hitachi, Ltd.) to determine the thickness of the shell layer (Q) of the core-shell particle (C) (or the comparative particle (C')) from the average of the thinnest and thickest portions thereof. Further, the thicknesses of the shell layers (Q) of any 100 core-shell particles (C) (or comparative particles (C')) were determined in the same manner as described above, and the average thereof was regarded as the average thickness of the shell layers (Q). Table 1 shows the results.

Examples 1 to 16 and Comparative Examples 1 to 4: Separation of Protein Using Core-Shell Particles (C)

The core-shell particles (C1-1) to (C1-16) obtained in Production Examples 1 to 16 and the comparative particles (C1'-1) to (C1'-4) obtained in Comparative Production Examples 1 to 4 were used for separation of the substance to be separated (D) (protein) from the sample (E) by the following method.

Solutions obtained by the separation operation were subjected to evaluation of "total protein concentration", "AFP concentration", and "AFP purity" by the following methods.

<Separation Operation: Extraction of AFP from Human Serum>

[Collection of Core-Shell Particles (C1)]

A 0.02 M phosphate buffer solution (5 mL) containing the core-shell particles (C1) obtained in the production example was contacted with a magnet from the outside of the vessel to magnetically collect the core-shell particles (C1), and the supernatant was directly removed. Thus, the core-shell particles (C1) were collected.

[Composite Formation Step]

Next, a human serum solution (10 mL) containing αfetoprotein (AFP) (1660 ng/mL) as the target substance was added to the reaction vessel containing the core-shell particles (C1) with the supernatant removed, followed by stirring with inversion for one hour. Thus, a composite (C1-AFP) of the core-shell particles (C1) and AFP was formed.

[Composite Separation Step]

After the reaction, the solution was contacted with a magnet from the outside of the vessel to magnetically collect the composite (C1-AFP), and the supernatant was directly removed. Thus, the composite (C1-AFP) was collected.

[Target Substance Dissociation Step]

A physiological saline solution (1 mL) containing 0.1 wt % Sannonic SS-120 (Sanyo Chemical Industries, Ltd.) was added to the reaction vessel containing the composite (C1-AFP) to disperse the particles. Subsequently, the particles were magnetically collected with a magnet, and the supernatant was removed. This washing operation was repeated twice.

Next, an 0.5 wt % aqueous sodium lauryl sulfate solution (0.25 mL) was added to the reaction vessel containing the particles, followed by stirring with inversion for one hour to dissociate the AFP from the composite (C1-AFP). The core-shell particles (C1) were magnetically collected with a magnet, and a supernatant (XA-1) was pipetted out. A 0.5 wt % aqueous sodium lauryl sulfate solution (0.25 mL) was added again to the reaction vessel containing the magnetically collected core-shell particles (C1), followed by stirring with inversion for one hour. Then, the particles were magnetically collected, and a supernatant (XB-1) was pipetted out. The supernatant (XA-1) and the supernatant (XB-1) were mixed, whereby a solution (X-1) containing AFP was obtained.

<Total Protein Concentration>

Using an ultraviolet-visible spectrophotometer "UV-1800" (Shimadzu Corporation), the absorbance (optical path length: 10 mm) of the solution (X-1) containing AFP was measured, and the total protein concentration was calculated from the following formula (assuming that the total protein concentration is 1 mg/mL when the absorbance at 280 nm is 1.0). Table 2 shows the results.

Total protein concentration (mg/mL)=absorbance at 280 nm (optical path length: 10 mm)

<AFP Concentration>

The solution (X-1) containing AFP was 1000-fold diluted with SphereLite analyte diluent (FUJIFILM Wako Pure Chemical Corporation), and the AFP concentration was measured using an automated chemiluminescent enzyme immunoassay machine "SphereLight Wako" (FUJIFILM Wako Pure Chemical Corporation). The obtained value was multiplied by 1000 to calculate the AFP concentration of the solution (X-1). Table 2 shows the results.

<AFP Purity>

The AFP purity was calculated by the following formula. Table 2 shows the results.

AFP purity (%)=AFP concentration/total protein concentration×100

TABLE 1

| | | | | Production Examples | | | | | | |
|---|---|---|---|---|---|---|---|---|---|---|
| | | | | 1 | 2 | 3 | 4 | 5 | 6 | 7 |
| | Core-shell particles (C) | | | C1-1 | C1-2 | C1-3 | C1-4 | C1-5 | C1-6 | C1-7 |
| | Surfactant used in production of core layers (P) | | | Emalmin 200 | Emalmin 200 | Emalmin 200 | Emalmin 200 | Emalmin 200 | Emalmin 200 | Emalmin 200 |
| Production conditions | Classification step | Centrifugation step 1 | Rotation speed (rpm) | 2800 | 2800 | 1600 | 1400 | 1600 | 1600 | 1600 |
| | | | Centrifugation time (min) | 1 | 1 | 1 | 1 | 1 | 1 | 1 |

TABLE 1-continued

| | | | | | | | | | |
|---|---|---|---|---|---|---|---|---|---|
| | | | Repetition number | 4 | 20 | 20 | 20 | 20 | 20 | 20 |
| | | Centrifugation step 2 | Rotation speed (rpm) | 600 | 600 | 800 | 1000 | 800 | 800 | 300 |
| | | | Centrifugation time (min) | 1 | 1 | 1 | 1 | 1 | 1 | 1 |
| | | | Repetition number | 1 | 1 | 1 | 1 | 1 | 1 | 1 |
| | | Washing step 1 | Repetition number | 10 | 10 | 10 | 10 | 10 | 10 | 10 |
| Magnetic metal oxide particles (A) | Volume average particle size (nm) of magnetic metal oxide particles (A) | | | 15 | 15 | 15 | 15 | 15 | 15 | 15 |
| Core layer (P) | Weight percent (wt %) of magnetic metal oxide particles (A) in core layer (P) | | | 83 | 83 | 83 | 83 | 83 | 83 | 83 |
| Core-shell particles (C) | Volume average particle size of core-shell particles (C) | | | 2.1 μm | 2.2 μm | 2.2 μm | 2.0 μm | 2.0 μm | 2.0 μm | 2.1 μm |
| | Coefficient of variation (C.V.) of particle size of core-shell particles (C) | | | 47% | 32% | 21% | 11% | 20% | 18% | 22% |
| | Average thickness of shell layers (Q) of core-shell particles (C) | | | 100 nm | 100 nm | 100 nm | 100 nm | 3 nm | 10 nm | 300 nm |
| | Average thickness of shell layers (Q)/particle size of core layer (P) | | | 0.053 | 0.050 | 0.050 | 0.056 | 0.0015 | 0.0051 | 0.20 |

| | | | | Production Examples | | | | | | |
|---|---|---|---|---|---|---|---|---|---|---|
| | | | | 8 | 9 | 10 | 11 | 12 | 13 | 14 |
| | Core-shell particles (C) | | | C1-8 | C1-9 | C1-10 | C1-11 | C1-12 | C1-13 | C1-14 |
| | Surfactant used in production of core layers (P) | | | Emalmin 200 | Emalmin 200 | Emalmin 200 | Emalmin 200 | Emalmin 200 | Emalmin 200 | Emalmin 200 |
| Production conditions | Classification step | Centrifugation step 1 | Rotation speed (rpm) | 1600 | 2000 | 400 | 1400 | 2800 | 2800 | 2800 |
| | | | Centrifugation time (min) | 1 | 10 | 1 | 1 | 1 | 1 | 1 |
| | | | Repetition number | 20 | 20 | 20 | 40 | 20 | 20 | 20 |
| | | Centrifugation step 2 | Rotation speed (rpm) | 800 | 1000 | 200 | 1300 | 600 | 600 | 600 |
| | | | Centrifugation time (min) | 1 | 10 | 1 | 1 | 1 | 1 | 1 |
| | | | Repetition number | 1 | 1 | 1 | 1 | 1 | 1 | 1 |
| | | Washing step 1 | Repetition number | 10 | 10 | 10 | 10 | 10 | 10 | 10 |

TABLE 1-continued

| | | | | | | | | |
|---|---|---|---|---|---|---|---|---|
| Magnetic metal oxide particles (A) | Volume average particle size (nm) of magnetic metal oxide particles (A) | 15 | 15 | 15 | 15 | 15 | 15 | 15 |
| Core layer (P) | Weight percent (wt %) of magnetic metal oxide particles (A) in core layer (P) | 83 | 83 | 83 | 83 | 63 | 92 | 83 |
| Core-shell particles (C) | Volume average particle size of core-shell particles (C) | 2.2 μm | 0.6 μm | 8.5 μm | 1.9 μm | 2.4 μm | 1.9 μm | 2.1 μm |
| | Coefficient of variation (C.V.) of particle size of core-shell particles (C) | 23% | 23% | 21% | 6% | 31% | 34% | 33% |
| | Average thickness of shell layers (Q) of core-shell particles (C) | 800 nm | 100 nm | 100 nm | 100 nm | 100 nm | 100 nm | 50 nm |
| | Average thickness of shell layers (Q)/particle size of core layer (P) | 1.3 | 0.25 | 0.012 | 0.059 | 0.045 | 0.059 | 0.025 |

| | | | Production Examples | | Comparative Production Examples | | | |
|---|---|---|---|---|---|---|---|---|
| | | | 15 | 16 | 1 | 2 | 3 | 4 |
| | Core-shell particles (C) | | C1-15 | C1-16 | C1'-1 | C1'-2 | C1'-3 | C1'-4 |
| | Surfactant used in production of core layers (P) | | Emalmin 200 | Emalmin 200 | NSA-17 | NSA-17 | Emalmin 200 | Emalmin 200 |
| Production conditions | Classification step | Centrifugation step 1 — Rotation speed (rpm) | 1200 | 600 | 2000 | 600 | 1600 | 1400 |
| | | Centrifugation time (min) | 5 | 1 | 10 | 10 | 1 | 1 |
| | | Repetition number | 20 | 20 | 20 | 20 | 20 | 40 |
| | Centrifugation step 2 | Rotation speed (rpm) | 800 | 200 | 200 | 300 | 800 | 1300 |
| | | Centrifugation time (min) | 5 | 1 | 10 | 10 | 1 | 1 |
| | | Repetition number | 1 | 1 | 1 | 1 | 1 | 1 |
| | Washing step 1 | Repetition number | 10 | 10 | 10 | 10 | 10 | 10 |
| Magnetic metal oxide particles (A) | Volume average particle size (nm) of magnetic metal oxide particles (A) | | 15 | 15 | 15 | 15 | 15 | 15 |
| Core layer (P) | Weight percent (wt %) of magnetic metal oxide particles (A) in core layer (P) | | 83 | 83 | 83 | 83 | 83 | 83 |
| Core-shell particles (C) | Volume average particle size of core-shell particles (C) | | 1.1 μm | 5.0 μm | 2.1 μm | 2.0 μm | 2.0 μm | 1.9 μm |
| | Coefficient of variation (C.V.) of particle size of core-shell particles (C) | | 30% | 35% | 112% | 65% | 21% | 6% |
| | Average thickness of shell layers (Q) of core-shell particles (C) | | 100 nm | 100 nm | 100 nm | 100 nm | None | None |
| | Average thickness of shell layers (Q)/particle size of core layer (P) | | 0.111 | 0.021 | 0.053 | 0.056 | — | — |

TABLE 2

| | | Examples | | | | | | | | | |
|---|---|---|---|---|---|---|---|---|---|---|---|
| | | 1 | 2 | 3 | 4 | 5 | 6 | 7 | 8 | 9 | 10 |
| | Core-shell particles (C) | C1-1 | C1-2 | C1-3 | C1-4 | C1-5 | C1-6 | C1-7 | C1-8 | C1-9 | C1-10 |
| | Substance (G) | Anti-AFP polyclonal antibody | | | | | | | | | |
| Purity | Total protein concentration (μg/mL) | 34.2 | 24.3 | 23.5 | 31.5 | 38.2 | 31 | 26.2 | 23.5 | 33.7 | 21.3 |
| | AFP concentration (μg/ml) | 18.3 | 20.1 | 20.3 | 20.2 | 20.7 | 19.9 | 21.5 | 19.0 | 17.5 | 11.9 |
| | Purity (%) | 54% | 83% | 86% | 64% | 54% | 64% | 82% | 81% | 52% | 56% |

| | | Examples | | | | | | Comparative Examples | | | |
|---|---|---|---|---|---|---|---|---|---|---|---|
| | | 11 | 12 | 13 | 14 | 15 | 16 | 1 | 2 | 3 | 4 |
| | Core-shell particles (C) | C1-11 | C1-12 | C1-13 | C1-14 | C1-15 | C1-16 | C1'-1 | C1'-2 | C1'-3 | C1'-4 |
| | Substance (G) | Anti-AFP polyclonal antibody | | | | | | Anti-AFP polyclonal antibody | | | |
| Purity | Total protein concentration (μg/mL) | 32.5 | 25.0 | 24.6 | 24.5 | 24.4 | 25.1 | 63.2 | 47.3 | 61.6 | 103.2 |
| | AFP concentration (μg/ml) | 17.5 | 20.2 | 20.4 | 19.9 | 19.9 | 20.3 | 16.8 | 18.1 | 17.1 | 16.9 |
| | Purity (%) | 54% | 81% | 83% | 81% | 82% | 81% | 27% | 38% | 28% | 16% |

As shown in Table 2, the solutions containing the substance to be separated (D) (AFP) obtained by the method of the present invention have a higher purity with lesser amounts of substances other than the substance to be separated (D) than the solutions containing the substance to be separated (D) obtained by the method using the comparative particles.

Examples 17 to 23 and Comparative Example 5: Separation of DNA Using Core-Shell Particles (C)

The core-shell particles (C-1) to (C-4) and (C-11) obtained in the classification step of the core-shell particles (PC) and the comparative particles (C'-2) obtained in the classification step of the core-shell particles (PC') in the above production Examples were subjected to measurement of the volume average particle size and coefficient of variation of the particle size of the core-shell particles (C) by the following methods, and the substance to be separated (D) (DNA) was separated from the sample (E).
<Method of Measuring Volume Average Particle Size and Coefficient of Variation of Particle Size of Core-Shell Particles (C)>
The volume average particle size and the coefficient of variation of the particle size of the core-shell particles (C-1) to (C-4) and (C-11) and the comparative particles (C'-2) were measured using phosphate buffer solutions containing the core-shell particles obtained in the production examples as samples, by a laser diffraction/scattering particle size distribution measuring device ("Microtrac MT3300" from MicrotracBEL Corp.). Table 3 shows the results.
[Retrieval of Core-Shell Particles (C)]
(1) The core-shell particles (296 mg) were placed in a glass container, and purified water (10 mL) was added to a sample bottle, followed by stirring using a vortex mixer, whereby a dispersion of the core-shell particles (C) was obtained.
(2) The dispersion of the core-shell particles (C) (600 μL) was collected in a 1.5-mL microtube, and the supernatant was removed.
[Composite Formation Step]
(3) A DNA aqueous solution (an aqueous solution obtained by dissolving DNA (deoxyribonucleic acid derived from salmon semen, FUJIFILM Wako Pure Chemical Corporation) at a concentration of 2.40 mg/ml in Tris-EDTA buffer (tris(hydroxymethyl)aminomethane: 10 mM; tetrasodium ethylenediaminetetraacetate: 2 mM; pH 7.86)) (150 μl) was mixed with a BSA aqueous solution (an aqueous solution obtained by dissolving BSA at a concentration of 2.40 mg/ml in Tris-EDTA buffer (tris(hydroxymethyl)aminomethane: 10 mM; tetrasodium ethylenediaminetetraacetate: 2 mM; pH 7.86)) (150 μl). The mixture was added as the sample (E) (a sample containing DNA as the target substance (D1) and BSA as impurities) to the microtube obtained in (2).
(4) An aqueous chaotropic salt solution (an aqueous solution obtained by dissolving a specific type of chaotropic salt described in Table 3 to give a concentration of 6 M in Tris-EDTA buffer ((tris(hydroxymethyl)aminomethane: 10 mM; tetrasodium ethylenediaminetetraacetate: 2 mM; pH 7.86)) (900 μl) was added to the microtube obtained in (3).
(5) The microtube obtained in (4) was shaken using a shaker incubator (37° C., 350 rpm, 2.0 hr). Thus, a composite (C-DNA) was obtained.
[Composite Separation Step]
(6) The supernatant in the microtube obtained in (5) was removed. Then, after a 70 vol % aqueous ethanol solution (900 μL) was added to disperse the particles, the particles were contacted with a magnet from the outside of the vessel to magnetically collect the composite (C-DNA), and the supernatant was directly removed. This washing operation was repeated 10 times. Thus, the composite (C-DNA) was collected.
[Target Substance Dissociation Step]
(7) Subsequently, Tris-EDTA buffer (tris(hydroxymethyl) aminomethane: 50 mM; tetrasodium ethylenediaminetetraacetate: 10 mM; pH 7.86) (400 μL) was added to the microtube obtained in (6). The mixture was stirred for 15 seconds every five minutes using a vortex mixer, and this operation was repeated three times. Thus, DNA and the like were dissociated from the composite (C-DNA). Subsequently, the core-shell particles (C) were magnetically collected with a magnet, the supernatant was pipetted out, and the solution containing DNA and the like was collected.
<Measurement of DNA Concentration and BSA Concentration>
[Pretreatment for Measurement]
The whole amount of the solution (100 μL) collected in (7) was added dropwise to a desalting and buffer exchange gravity column (PD-10 from GE Healthcare). Then, using purified water as an eluent, samples for DNA concentration measurement and for BSA concentration measurement were obtained.

Specifically, first, the solution (100 µL) collected in (7) was added to the column. Subsequently, purified water (1100 µL) as an eluent was added to the column, and an eluent discharged by gravity flow was collected with a microtube. This operation was repeated six times. The microtube used for collection was replaced every time.

The solution in the microtube obtained in the third to sixth operation to elute DNA was extracted in portions (200 µL each), and these portions were mixed at equal volume to obtain a DNA solution. The concentration of the DNA solution was measured by the following method.

Likewise, the solution in the microtube obtained in the third to sixth operation to elute BSA was extracted in portions (200 µL each), and these portions were mixed at equal volume to obtain a BSA solution. The concentration of the BSA solution was measured by the following method.

[Measurement of DNA Concentration]

The absorbance at 260 nm was measured using a spectrophotometer.

A calibration curve showing the relationship between the concentration and the absorbance was made using DNA standard solutions of known concentrations (deoxyribonucleic acid derived from salmon semen, FUJIFILM Wako Pure Chemical Corporation), and the concentration of the DNA described above was determined using the calibration curve. Table 3 shows a value obtained by converting the concentration of the DNA in the solution collected in (7) based the above value.

[Measurement of BSA Concentration]

Reagent A, Reagent B, and Reagent C from Micro BCATM Protein Assay Lit (THERMO Fisher Scientific) were mixed at a ratio of 25:24:1 to obtain a mixture (M).

The mixture (M) (100 µL) was added to a BSA solution (100 µL), and the resulting mixture was left standing at 37° C. for two hours.

Two hours later, the mixture that had been left standing was dispensed in an amount of 100 µL per hole of a 96-hole plate (Becton, Dickinson and Company Japan). Then, the absorbance was measured at an absorbance of 562 nm using a plate reader (MTA-32 from Corona Electric Co., Ltd.).

A calibration curve showing the relationship between the concentration and the absorbance was made using BSA standard solutions of known concentrations, and the concentration of the BSA described above was determined using the calibration curve. Table 3 shows a value obtained by converting the concentration of the BSA in the solution collected in (7) based the above value.

TABLE 3

| | Examples | | | | | | | Comparative Example |
|---|---|---|---|---|---|---|---|---|
| | 17 | 18 | 19 | 20 | 21 | 22 | 23 | 5 |
| Core-shell particles (C) | C-1 | C-2 | C-3 | C-4 | C-11 | C-3 | C-3 | C'-2 |
| Volume average particle size of core-shell particles (C) | 2.1 µm | 2.2 µm | 2.2 µm | 2.0 µm | 1.9 µm | 2.2 µm | 2.2 µm | 2.0 µm |
| Coefficient of variation (C.V.) of particles size of core-shell particles (C) | 47% | 32% | 21% | 11% | 6% | 21% | 21% | 65% |
| Average thickness of shell layers (Q) of core-shell particles (C) | 100 nm | 100 nm | 100 nm | 100 nm | 100 nm | 100 nm | 100 nm | 100 nm |
| Average thickness of shell layers (Q)/particle size of core layer (P) | 0.053 | 0.050 | 0.050 | 0.056 | 0.059 | 0.050 | 0.050 | 0.056 |
| Chaotropic salt | Guanidinium thiocyanate | Guanidinium thiocyanate | Guanidinium thiocyanate | Guanidinium thiocyanate | Guanidinium thiocyanate | Guanidine hydrochloride | Sodium perchlorate | Guanidinium thiocyanate |
| DNA concentration (µg/m$^2$) | 372 | 440 | 464 | 363 | 335 | 230 | 261 | 136 |
| BSA concentration (µg/m$^2$) | 68.0 | 18.0 | 7.0 | 55.0 | 53.0 | 10.0 | 8.0 | 135.0 |
| Purity (%) | 85% | 96% | 99% | 87% | 86% | 96% | 97% | 50% |

As shown in Table 3, each solution containing the substance to be separated (D) (DNA) obtained by the method of the present invention has a higher purity with a lesser amount of a substance (BSA) other than the substance to be separated (D) than the solution containing the substance to be separated (D) obtained by the method using the comparative particles.

INDUSTRIAL APPLICABILITY

The method of separating a substance to be separated using the core-shell particles of the present invention can be used in a wide range of applications such as purification of proteins (e.g., antibodies and antigens), purification of RNA and DNA, and removal of cells and viruses. The method is useful in that it is applicable to purification of raw materials of pharmaceutical products and the like and extraction of analytes in diagnosis and the like.

In particular, when the substance to be separated (D) is the target substance (D1), the final purified product has a high purity and is thus highly suitable for purification of raw materials of pharmaceutical products and the like.

The invention claimed is:

1. A plurality of core-shell particles (C), each core-shell particle (C) comprising:
    a core layer (P) as a matrix of silica particles containing magnetic metal oxide particles (A); and
    a Shell layer (Q) that is a silica layer on a surface of the core layer (P), an average thickness the shell layer (Q) in the plurality of core-shell particles (C) being 3 to 3000 nm,
    wherein a weight percentage of the magnetic metal oxide particles (A) in the core layer (P) is 60 to 95 wt % based on a weight of the core layer (P), and
    the plurality of core-shell particles (C) have a particle size distribution with a coefficient of variation of 21 to 50%.

2. The plurality of core-shell particles according to claim 1,
    wherein the plurality of core-shell particles (C) have a particle size distribution with a coefficient of variation of 21 to 35%.

3. The plurality of core-shell particles according to claim 1,
wherein the magnetic metal oxide particles (A) have a volume average particle size of 1 to 50 nm.

4. The plurality of core-shell particles according to claim 1,
wherein the plurality of core-shell particles (C) have a volume average particle size of 0.5 to 20 μm.

5. The plurality of core-shell particles according to claim 1,
wherein the magnetic metal oxide particles (A) contain iron oxide.

6. A separation and purification method of separating a substance to be separated (D) from a sample (E),
wherein the plurality of core-shell particles (C) according to claim 1 are used.

7. The separation and purification method according to claim 6,
wherein the substance to be separated (D) is a target substance (D1), the method comprising:
a composite formation step of forming a composite (F1) of the plurality of core-shell particles (C) and the target substance (D1) by contacting a sample (E1) containing the target substance (D1) with the plurality of core-shell particles (C),
a composite separation step of separating the composite (F1) from the sample (E1) by a magnetic force; and
a target substance dissociation step of dissociating the target substance (D1) from the composite (F1) to obtain the target substance (D1).

8. The separation and purification method according to claim 7,
wherein the method comprises a core-shell particle retrieving step of retrieving the plurality of core-shell particles (C) after the target substance dissociation step.

9. The separation and purification method according to claim 8,
wherein the composite formation step, the composite separation step, and the target substance dissociation step are performed after the core-shell particle retrieving step, using the plurality of the core-shell particles (C) retrieved.

10. The separation and purification method according to claim 6,
wherein the substance to be separated (D) is a non-target substance (D2), the step comprising:
a composite formation step of forming a composite (F2) of the plurality of the core-shell particles (C) and the non-target substance (D2) by contacting a sample (E2) containing a target substance (D1) and the non-target substance (D2) with the plurality of core-shell particles (C); and
a non-target substance removal step of removing the non-target substance (D2) from the sample (E2) by separating the composite (F2) from the sample (E2) by a magnetic force to obtain a sample (E21) containing the target substance (D1).

11. The separation and purification method according to claim 10,
wherein the method comprises a core-shell particle retrieving step of retrieving the plurality of core-shell particles (C) from the composite (F2), after the non-target substance removal step.

12. The separation and purification method according to claim 11,
wherein the composite formation step and the non-target substance removal step are performed after the core-shell particle retrieving step, using the plurality of core-shell particles (C) retrieved.

13. The separation and purification method according to claim 10,
wherein the non-target substance (D2) comprises multiple types of non-target substances.

14. The separation and purification method according to claim 6,
wherein the substance to be separated (D) is at least one selected from the group consisting of a DNA, an RNA, a cell, a virus, a bacterium, and a protein.

15. The separation and purification method according to claim 6,
wherein the core-shell particles (C) are core-shell particles (C1) each having a surface with a substance (G) immobilized thereon, the substance (G) being capable of binding to the substance to be separated (D).

16. The separation and purification method according to claim 15,
wherein the substance (G) contains a functional group (J) that binds to the substance to be separated (D).

17. The separation and purification method according to claim 16,
wherein the functional group (J) is at least one group selected from the group consisting of an amino group and an ammonium group.

* * * * *